United States Patent [19]
Doi

[11] Patent Number: 6,033,359
[45] Date of Patent: Mar. 7, 2000

[54] ENDOSCOPIC LENGTH-MEASURING TOOL

[75] Inventor: Yuzuru Doi, Saitama, Japan

[73] Assignee: Asahi Kogaku Kogyo Kabushiki Kaisha, Tokyo, Japan

[21] Appl. No.: 09/179,615

[22] Filed: Oct. 27, 1998

[30] Foreign Application Priority Data

Oct. 28, 1997 [JP] Japan ..................................... 9-333448
Aug. 27, 1998 [JP] Japan ................................... 10-241734

[51] Int. Cl.[7] .................................................. A61B 5/103
[52] U.S. Cl. .......................... 600/117; 600/104; 600/587; 606/1
[58] Field of Search ..................................... 600/101, 104, 600/106, 117, 118, 127, 129, 153, 587; 606/1, 198; 604/104, 105, 106, 107, 108; 33/511, 512, 700

[56] References Cited

U.S. PATENT DOCUMENTS 5,058,603  10/1991  Doi et al. .
5,309,894  5/1994   Heckele et al. .

FOREIGN PATENT DOCUMENTS 0526721  2/1993   European Pat. Off. .
0818180  1/1998   European Pat. Off. .
3926320  3/1990   Germany .
6-44401  11/1994  Japan .

*Primary Examiner*—Linda C. M. Dvorak
*Assistant Examiner*—Brad C. Blaise
*Attorney, Agent, or Firm*—Greenblum & Bernstein, P.L.C.

[57] ABSTRACT

An endoscopic length-measuring tool for measuring the size of a diseased part within patient's body cavity. A plurality of splits are formed in a front end portion of a flexible tube of the tool so as to extend in parallel to an axial direction of the tube and to have equal lengths. Each of the plurality of strips is defined between adjacent splits. Radially outwardly bendable portions and radially inwardly bendable portions are formed on each strip. An operating wire is axially and movably disposed within the tube. The front end of the operating wire is retained on a portion of the tube located forwardly from the splits. When the operating wire is moved axially and rearwardly relative to the tube, the strips are bent at the bendable portions and spread radially outwardly, so that a length-measuring section on the strip is disposed within an observation visual field of an endoscope.

10 Claims, 2 Drawing Sheets

ENDOSCOPIC LENGTH-MEASURING TOOL

BACKGROUND OF THE INVENTION a) Field of the Invention

The present invention relates to an endoscopic length-measuring tool adapted to pass through a forceps channel to measure a size of a diseased part or the like within a body cavity.

b) Description of Related Art

The present inventor previously proposed a related endoscopic length-measuring tool, as disclosed in Japanese Utility Model Kokoku Publication No. Hei. 6-44401. The proposed length-measuring tool is advantageous over other available endoscopic length-measuring tools because it is simple in structure, and can be used in combination with various endoscopes.

This related length-measuring tool has two splits formed in a portion at a predetermined distance near a front end of a flexible sheath. The splits extend in a direction perpendicular to an axial direction of the sheath. The portion in which the two splits are formed is protruded from the front end of an endoscope, and bent into a T-shape with the aid of the two splits, so that a scale on the bent portion (i.e., a length-measuring section) can be observed through an endoscope.

The proposed length-measuring tool, which uses the T-shaped bent portion as a length-measuring section has a drawback. That is, since the length-measuring section is in the form of a single bar, if a rotational direction of the length-measuring tool relative to the endoscope is not appropriate, the length-measuring section will not be within observation visual field of the endoscope. Adjustment of the rotational direction of the length-measuring tool is difficult after the tool is passed through the endoscope. It is often required to repeatedly insert and remove the length-measuring tool into and out of the forceps channel of the endoscope until the rotational direction of the tool is acceptable.

SUMMARY OF THE INVENTION

An object of the present invention is to provide an endoscopic length-measuring tool that can facilitate the size measurement of patient's diseased part. That is, it is an object of the present invention to provide an endoscopic length-measuring tool that does not require an operator or a doctor to repeatedly insert and remove the length-measuring tool into and out of a forceps channel of an endoscope.

An endoscopic length-measuring tool according to the present invention has the following novel arrangement. A plurality of equal-length splits is formed in a front end portion of a flexible tube of the tool so as to extend in parallel to an axial direction of the tube. A plurality of strips are respectively defined between adjacent splits. Radially outwardly bendable portions and radially inwardly bendable portions are formed on each strip. An operating wire is axially and movably disposed within the tube. The front end of the operating wire is retained on a portion of the tube located forwardly of the splits. When the operating wire is moved axially and rearwardly relative to the tube, the strips are bent at the bendable portions and spread radially outwardly, so that a length-measuring section on the strip is disposed within an observation visual field of an endoscope.

The present disclosure relates to the subject matter contained in Japanese patent application Nos. Hei. 9-333448 (filed on Oct. 28, 1997) and Hei. 10-241734 (filed on Aug. 27, 1998), which are expressly incorporated herein by reference in their entireties.

DETAILED DESCRIPTION OF THE PREFERRED EMBODIMENT

Figure 1:
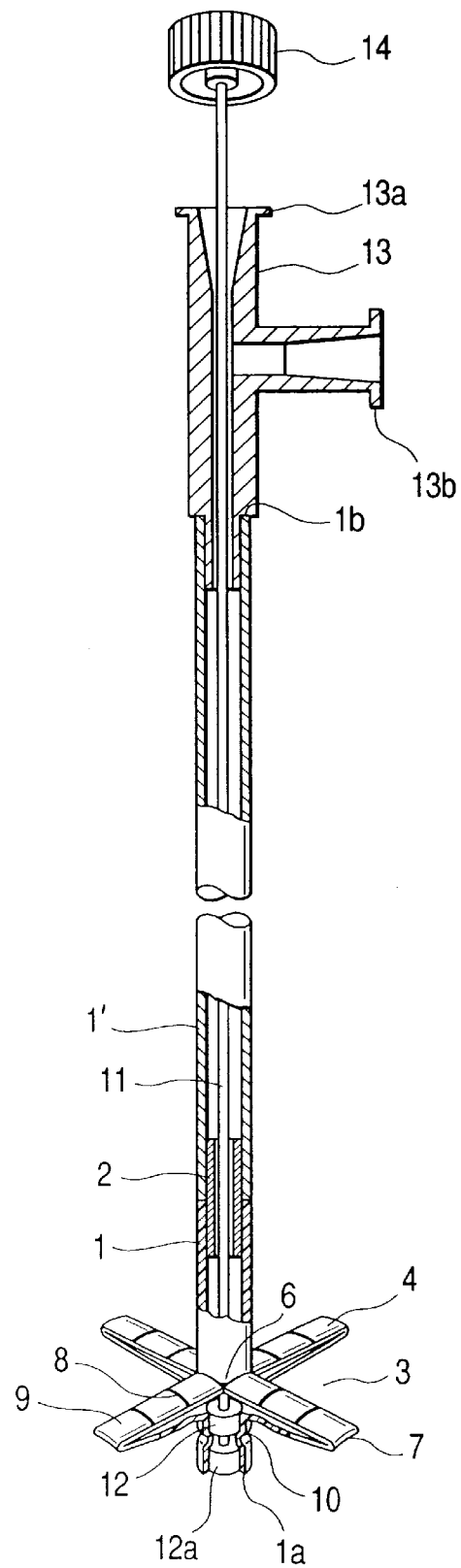
FIG. 1 is a sectional, perspective view showing an endoscopic length-measuring tool of the present invention.
Figure 2:
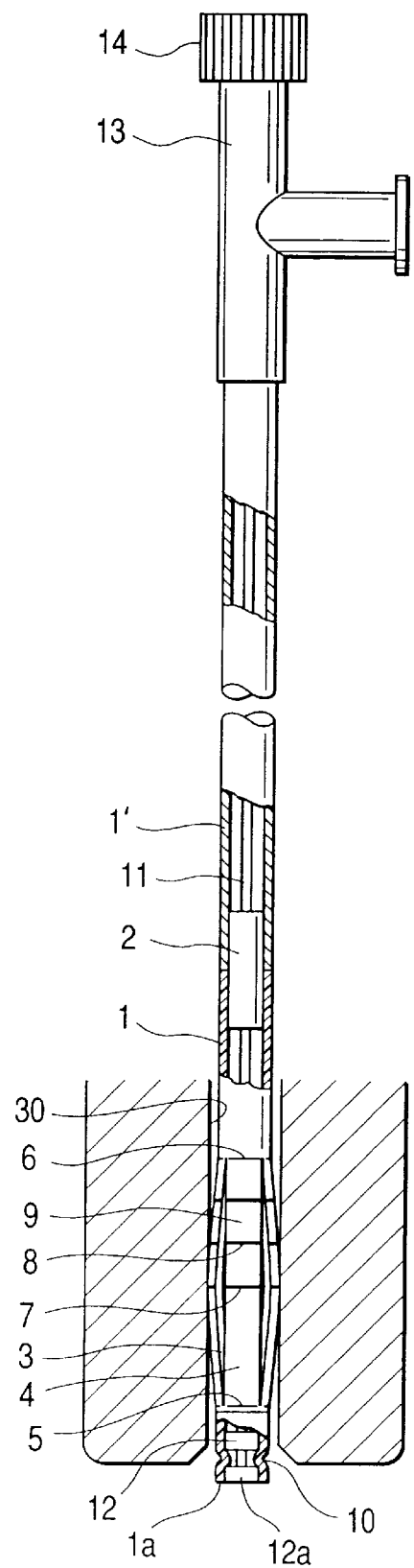
FIG. 2 is a partially sectional side view showing the endoscopic length-measuring tool of FIG. 1 being passed through a forceps channel of an endoscope.

The endoscopic length-measuring tool according to the present invention will be described with reference to the accompanying drawings. FIG. 1 shows the endoscopic length-measuring tool, and FIG. 2 shows a state in which the length-measuring tool is passed through a forceps channel 30 of an endoscope.

A sheath of the length-measuring tool that is insertable into the forceps channel 30 is constructed of a plurality of sections including a flexible tube 1 at a front end 1a, a flexible pipe 1' at a rear end 1b, and a connecting tube 2 connecting the tube 1 and the pipe 1' together. Alternatively, the sheath may be formed solely of a flexible tube 1 extending over the entire length of the tool.

The flexible tube 1 is prepared, for example, such that a tetrafluoroethylene resin tube having an outer diameter of 1.5 to 2.5 mm and a radial thickness of 0.2 to 0.4 mm is cut to a length of 20 to 50 mm. As for the flexible pipe 1', a material having an appropriate strength is preferably used. A coil pipe formed by winding stainless steel spirally and closely to thereby provide a constant diameter may also be used.

Four longitudinal splits 3 of equal length are formed in a portion of the flexible tube 1 in the vicinity of the front end 1a of the tube 1. Each of the four longitudinal splits 3 extends in parallel to the axial direction of the flexible tube 1. As a consequence of the provision of the four splits 3, a strip 4 is formed between each adjacent pair of the splits 3. The four splits 3 are formed at substantially constant angular intervals of 90° in the wall of the flexible tube 1.

The flexible tube 1 is further formed using first and second radially outwardly bendable portions 5 and 6 at front and rear ends of each strip 4, and a radially inwardly bendable portion 7 at a middle portion between the ends of each strip 4.

A scale 8 is provided on an outer surface of each strip 4 between the radially inwardly bendable portion 7 and the second radially outwardly bendable portion 6 located closer to the operator than the bendable portion 7. This portion of each strip 4, between the second radially outwardly bendable portion 6 and the radially inwardly bendable portion 7, forms a length measurement section 9. The length of the length measurement section 9 can be set as desired by changing the length of the split 3.

A flexible operating wire 11 is disposed to be axially movable within the sheath 1,1',2. The length of the flexible operating wire 11 is slightly longer than the length of the sheath 1,1',2. Two stoppers 12 and 12a are projectingly provided on the front end of the operating wire 11 with a predetermined distance between the two stoppers 12,12a. A constriction 10 formed on the front end of the flexible tube 1 is clamped between the two stoppers 12 and 12a, and is fixed by adhesive, caulking or the like. The constriction 10 may be fixed in such a manner that the constriction 10 is clamped between the stoppers 12 and 12a to prohibit the removal of the operating wire 11 in the axial direction, while permitting the rotation of the operating wire 11 about its axis. With this arrangement, the front end of the operating wire 11 is retained on the front end of the flexible tube 1.

As for the operating wire 11, an optical fiber having a diameter of about 0.6 mm to 1 mm is preferably used. Such dimensions provide an excellent flexibility and prevent permanent deformation. A stranded wire of stainless steel may alternatively be used.

The scale 8 can be formed, for example, by painting lines in a cylindrical manner on the outer surface of the flexible tube 1. The scale 8 in the illustrated example is applied to divide the length measurement section 9 into three equal length segments. However, the scale 8 may be modified in various manners depending on the intended use of the length-measuring tool.

A plastic or metal cap 13 is fixed to the rear end 1b of the flexible pipe 1' so that the inside of the cap 13 is communicated with the inside of the flexible pipe 1'. The cap 13 has a first lure lock cap 13a linearly arranged with respect to the flexible pipe 1' and a second lure lock cap 13b protruding from a side face of the flexible pipe 1'.

An operation knob 14 is attached to the rear end of the operating wire 11 and disposed on the first lure lock cap 13a so that the operation knob 14 may be engaged with and disengaged from the first lure lock cap 13a. To move the operating wire 11 axially within the sheath 1,1',2, the operation knob 14 is disengaged from and moved axially relative to the first lure lock cap 13a. The second lure lock cap 13b can be used, for example, such that an injector for injecting a cleaning solution is connected thereto for cleaning and disinfecting within the sheath 1,1',2.

Next, the manner of using the thus constructed endoscopic length-measuring tool will be described.

During the insertion of the endoscopic length-measuring tool into a forceps channel 30 of an endoscope, the operation knob 14 is engaged with the first lure lock cap 13a. This engagement results in the length measuring section 9 being linearly aligned with the sheath 1,1',2 and thus facilitates the insertion work of the tool into the forceps channel and the patient's body cavity.

To measure the size of the patient's diseased part, the front end portion of the flexible tube 1 is protruded from the front end of the endoscope, and then the operation knob is disengaged from the first lure lock cap 13a and pulled rearwardly. With the aid of bendable portions 5, 6 and 7 and splits 3, the strips 4 are spread into a cross-shape (X-shape) as shown in FIG. 1. This spreading is done in a manner such that at least one of four length measuring sections 9 is disposed within a visual field, which can be observed through an observation optical system (not shown) of the endoscope.

To remove the length-measuring tool from the forceps channel of the endoscope after the measurement is completed, the operation knob 14 is engaged with the first lure lock cap 13a so as to push the operating wire 11. As a result, the sheath 1,1',2 is pulled rearwardly.

During this removal of the length-measuring tool from the forceps channel, the strips 4 are contracted to extend straight along the axial direction, and thus the strips 4 in this state are easily inserted into the forceps channel 30. The further pulling of the flexible tube 1 completes the removal of the length-measuring tool from the forceps channel 30.

Although the illustrated example of the length-measuring tool has four strips 4, the invention is not limited thereby. A length-measuring tool of the present invention is preferably provided with at least three strips 4 (i.e., at least three splits 3) so that the spread length-measuring section 9 can be surely disposed within an observation visual field of an endoscope.

What is claimed is:

1. An endoscopic length-measuring tool comprising:
   a flexible tube having front and rear end portions;
   a plurality of splits formed in said front end portion, said splits extending in parallel to an axial direction of said tube and having equal lengths;
   a plurality of strips respectively defined between adjacent two of said splits;
   first and second bendable portions respectively located at front and rear ends of each of said strips, each of said first and second bendable portions being bendable radially outwardly;
   a third bendable portion located at a middle portion of each of said strips between said first and second bendable portions, each of said third bendable portions being bendable radially inwardly;
   an operating wire located in said tube and being movable axially relative to said tube, said operating wire having a front end retained on a retained portion of said tube located forwardly from said splits; and
   length-measuring sections provided on said strips.

2. An endoscopic length-measuring tool according to claim 1, wherein when said operating wire is moved axially and rearwardly relative to said tube, said strips are bent at said first, second and third portions and spread radially outwardly.

3. An endoscopic length-measuring tool according to claim 1, wherein each of said length-measuring sections is located between said second and third bendable portions.

4. An endoscopic length-measuring tool according to claim 1, further comprising:
   a flexible pipe connected to said rear end of said tube;
   a cap provided on a rear end of said flexible pipe; and
   an operation knob attached to a rear end of said operating wire, said operation knob being engageable with said cap.

5. An endoscopic length-measuring tool according to claim 4, wherein when said operation knob is engaged with said cap, said strips are contracted to extend in parallel to said axial direction of said tube.

6. An endoscopic length-measuring tool according to claim 1, wherein said plurality of splits comprises at least three splits, at least three of said splits being provided at substantially constant angular intervals.

7. An endoscopic length-measuring tool according to claim 1, wherein a scale is provided on each of said strips so as to be located between said second and third bendable portions.

8. An endoscopic length-measuring tool according to claim 1, further comprising:
   two stoppers provided projectingly on said front end of said operating wire and distanced from each other;
   a constriction provided on said retained portion of said tube, said constriction being clamped and retained between said two stoppers.

9. An endoscopic length-measuring tool according to claim 1, further comprising a flexible pipe connected to said rear end of said tube, and insertable into a forceps channel of an endoscope.

10. An endoscopic length-measuring tool according to claim 1, wherein said operating wire is an optical fiber of monofilament.

* * * * *